(12) United States Patent
Scherbring

(10) Patent No.: US 8,327,693 B2
(45) Date of Patent: Dec. 11, 2012

(54) MOBILE TURF INSTRUMENT APPARATUS HAVING DROPPABLE HAMMER TYPE ACCELEROMETER CARRIED ON ROTATING ARM

(75) Inventor: David J. Scherbring, Savage, MN (US)

(73) Assignee: The Toro Company, Bloomington, MN (US)

(*) Notice: Subject to any disclaimer, the term of this patent is extended or adjusted under 35 U.S.C. 154(b) by 89 days.

(21) Appl. No.: 13/035,937

(22) Filed: Feb. 26, 2011

(65) Prior Publication Data

US 2011/0203356 A1    Aug. 25, 2011

Related U.S. Application Data

(60) Continuation-in-part of application No. 12/606,754, filed on Oct. 27, 2009, which is a division of application No. 11/986,552, filed on Nov. 21, 2007, now Pat. No. 7,628,059.

(60) Provisional application No. 60/860,583, filed on Nov. 22, 2006.

(51) Int. Cl.
   *G01N 3/00* (2006.01)
(52) U.S. Cl. .......................................... 73/84
(58) Field of Classification Search ........................ None
   See application file for complete search history.

(56) References Cited

U.S. PATENT DOCUMENTS

| 3,477,283 A * | 11/1969 | Terry ................................. 73/84 |
| 5,479,992 A * | 1/1996 | Bassett ............................. 172/4 |
| 5,709,271 A * | 1/1998 | Bassett ............................. 172/4 |
| 7,628,059 B1 | 12/2009 | Scherbring |

FOREIGN PATENT DOCUMENTS

| GB | 1524445 | 9/1978 |
| JP | 1226912 | 9/1989 |
| JP | 401226912 | * 9/1989 |
| MX | GT06000012 | 1/2008 |

* cited by examiner

*Primary Examiner* — Robert R Raevis
(74) *Attorney, Agent, or Firm* — James W. Miller

(57) ABSTRACT

A mobile turf instrument apparatus has a wheeled frame that may be propelled over the ground by a motive device, such as by a separate vehicle or by its own engine and drive train. A driven arm is carried on the frame and revolves in circles to periodically insert the probe(s) of a probe assembly into the ground during motion of the frame. The drive to the arm is momentarily disengaged when the probe(s) of the probe assembly are inserted into the ground. The probe assembly comprises two parts that rock relative to one another. Two soil measurement devices are connected to the probe assembly. A soil moisture sensor is coupled to the probe assembly for measuring soil moisture when the probe(s) are inserted into the ground. A load cell is responsive to the amount of rocking of the two parts of the probe assembly to measure soil compaction.

15 Claims, 13 Drawing Sheets

MOBILE TURF INSTRUMENT APPARATUS HAVING DROPPABLE HAMMER TYPE ACCELEROMETER CARRIED ON ROTATING ARM

CROSS REFERENCE TO RELATED APPLICATIONS

This application is a continuation-in-part of application Ser. No. 12/606,754 filed Oct. 27, 2009, which is a division of application Ser. No. 11/986,552 filed Nov. 21, 2007, now U.S. Pat. No. 7,628,059, which claims the benefit of one or more previously filed copending provisional applications identified as follows: Application Ser. No. 60/860,583 filed Nov. 22, 2006.

TECHNICAL FIELD

This invention relates generally to the field of turf maintenance equipment. More particularly, this invention relates to equipment carrying instruments for measuring various parameters related to the health of the turf, such as soil moisture, soil compaction, etc.

BACKGROUND OF THE INVENTION

The turf maintenance field involves a wide range of equipment used to promote turf growth and to thereafter maintain the grass surface forming the upper portion of the turf. For example, aerators are used to punch holes in the ground to relieve soil compaction in and beneath the turf. Mowers are used to cut the grass surface of the turf to a desired height. Fertilizers apply nutrients and pesticides to the turf to encourage grass growth and to prevent or limit damage to the grass by insects.

In order to intelligently diagnose the health of the turf, various measuring instruments are used to measure various parameters related to the health of the turf. For example, many known soil moisture sensors determine the moisture content of the soil using Timed Domain Reflectometry (TDR). A TDR sensor involves sticking a probe assembly comprising various probes into the ground. When the probes are pulsed with electrical energy while they are inserted into the ground, a reading can be taken from which the moisture content of the soil can be derived.

A penetrometer is a type of instrument used to measure soil compaction. Like the TDR sensor described above, a penetrometer has a probe assembly that must be pushed into the ground in order for the penetrometer to take a reading. The penetrometer includes a load cell that measures the resistance the probe assembly encounters when entering the ground. This resistance is a measure of how compacted the soil is at the spot where the probe assembly has been inserted into the ground.

Other turf measurement instruments are known. A spectrometer known as the GreenSeeker® uses light emitting diodes (LED) to generate red and near infrared (NIR) light. The light generated is reflected off of the grass surface of the turf and is measured by a photodiode. Red light is absorbed by plant chlorophyll as an energy source during photosynthesis. Therefore, healthy turf absorbs more red light and reflects larger amounts of NIR than turf that is unhealthy. Thus, the GreenSeeker® Instrument provides a measurement of the health or vigor of the turf. Other spectrometers besides the GreenSeeker® are also known in the art.

A turf measurement instrument like the GreenSeeker® spectrometer operates without requiring physical penetration of the ground. A spectrometer works simply by shining light at the turf and measuring the reflected light from the grass. Thus, in the past a spectrometer type instrument has simply been mounted on a mobile frame and driven over an area of turf whose health is to be measured.

However, for a TDR soil moisture sensor, the probe assembly must be inserted into the ground in order for the device to operate. Thus, in the past, such an instrument has traditionally been hand held with the probe assembly being manually inserted or pushed into the soil at various desired spots. This is done by a walking operator who holds the instrument in his or her hands and who manually pushes the probe assembly into the soil to undertake a soil moisture measurement and then manually pulls the probe assembly out of the soil at the conclusion of the measurement. This is a difficult and tiring task. Moreover, when measuring the soil moisture content over a large area of turf, such as a golf course, it is extremely time consuming and laborious.

Penetrometers used to measure soil compaction have in the past been mounted on vehicles rather than being hand-held. However, like a TDR soil moisture sensor, the probe assembly of the penetrometer must be inserted into the ground in order to take a reading. Thus, with a vehicle mounted penetrometer, the vehicle must be stopped at each location where a reading is desired, the penetrometer must then be inserted into the ground, the reading is then taken, and then the penetrometer must be pulled out of the ground, all with the vehicle remaining stopped. Then, and only then, can the vehicle be driven to the next spot where a reading is to be taken. While the operator need not walk the entire area to be measured, the need to stop the vehicle at each spot where the penetrometer is to be inserted into the ground still makes the act of measuring a large area of turf a time consuming one.

SUMMARY OF THE INVENTION

One aspect of this invention relates to a mobile instrument for measuring a parameter of a turf, soil or ground surface. The apparatus comprises a frame supported for movement over the surface. An arm is carried on the frame for rotation about a first substantially horizontal axis of rotation. The arm has repeating cycles of rotation about the first axis of rotation as the frame is moved over the surface. An assembly is carried on the arm for rotation about a second substantially horizontal axis of rotation. The assembly rotates in a direction that is opposite to a direction in which the arm is rotating such that the assembly is self-leveling on the arm. The assembly is configured to engage with the surface during each cycle of rotation of the arm. An instrument is carried on the assembly for measuring the parameter of the surface from data arising from each engagement of the assembly with the surface.

Another aspect of this invention relates to a mobile measurement apparatus for measuring compaction or hardness of a turf, soil or ground surface. The apparatus comprises a frame supported for movement over the surface. An impact hammer is carried on the frame. The hammer is equipped with an instrument for providing data arising from impact of the hammer with the surface which data is indicative of compaction or hardness of the surface. A drive is carried on the frame and coupled to the hammer for elevating the hammer relative to the frame and for allowing the hammer to vertically drop downwardly relative to the frame under the influence of gravity with a bottom of the hammer impacting against the surface at an end of each drop to provide the compaction or hardness data for a spot on the surface impacted by the hammer. The drive being configured to automatically produce multiple sequential elevations and drops of the hammer in repeating cycles of operation as the frame traverses the surface without requiring the motion of the frame to be stopped and without requiring an operator to manually trigger or initiate the hammer elevations and drops.

An additional aspect of this invention relates to a mobile measurement apparatus for measuring compaction or hardness of a turf, soil or ground surface. The apparatus comprises a frame supported for movement over the surface. A revolving arm is carried on the frame for rotation about a substantially horizontal axis of rotation, the revolving arm being rotated in repeating 360° revolutions about the axis of rotation as the frame is moved over the surface. An elongated guide is rotatably carried on the revolving arm such the elongated guide remains substantially vertical during rotation of the arm. An impact hammer is vertically slidable on the guide with the hammer being configured to vertically drop downwardly on the guide under the influence of gravity during a first portion of each revolution of the arm such that a bottom of the hammer impacts against the surface once during each revolution of the arm. The hammer is equipped with an instrument for providing data arising from impact of the hammer with the surface which data is indicative of compaction or hardness of the surface.

BRIEF DESCRIPTION OF THE DRAWINGS

This invention will be described hereafter in the Detailed Description, taken in conjunction with the following drawings, in which like reference numerals refer to like elements or parts throughout.

DETAILED DESCRIPTION

Figure 1:
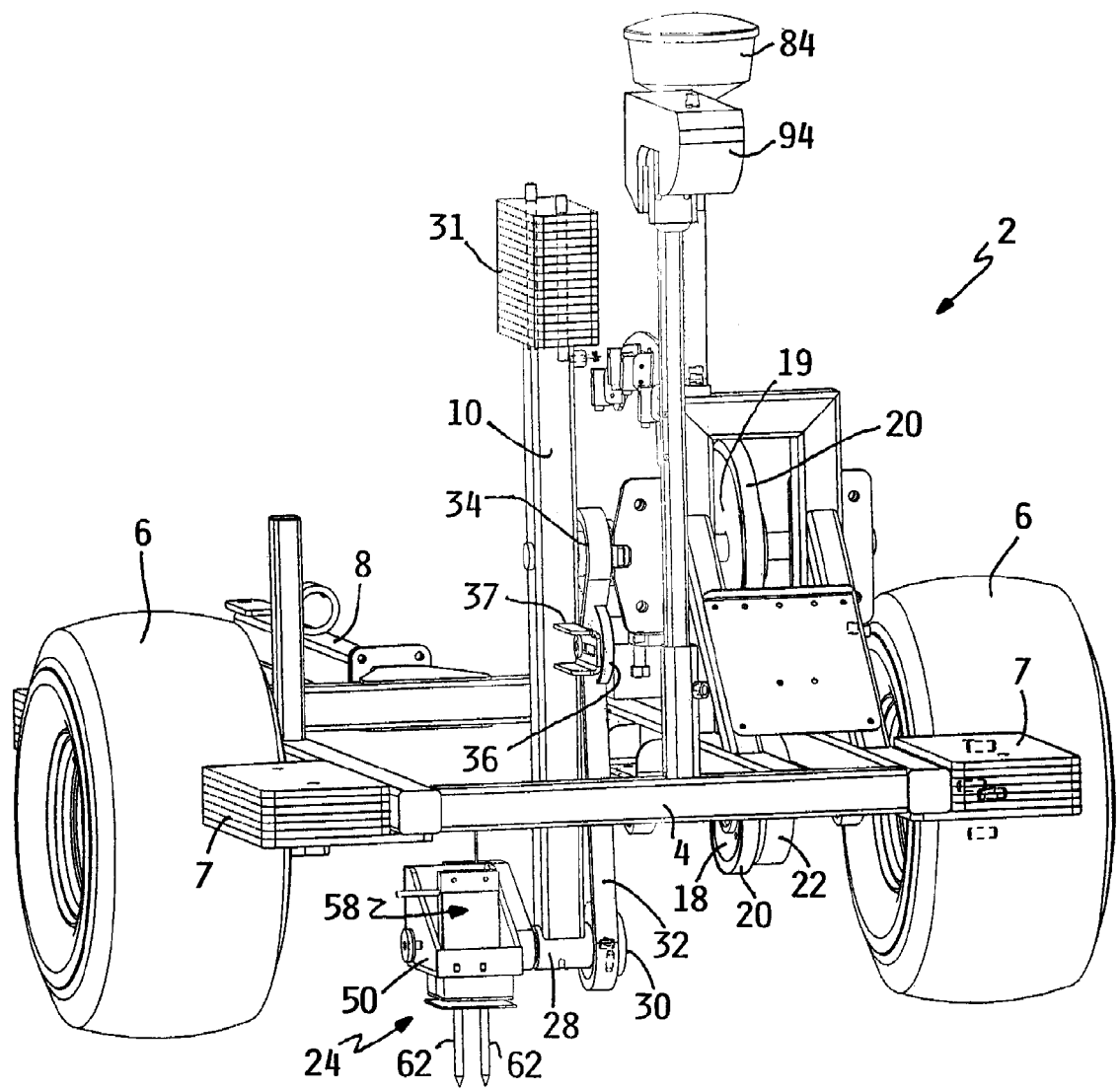
FIG. 1 is a perspective view towards the rear of one embodiment of a mobile turf instrument apparatus according to this invention.
Figure 2:
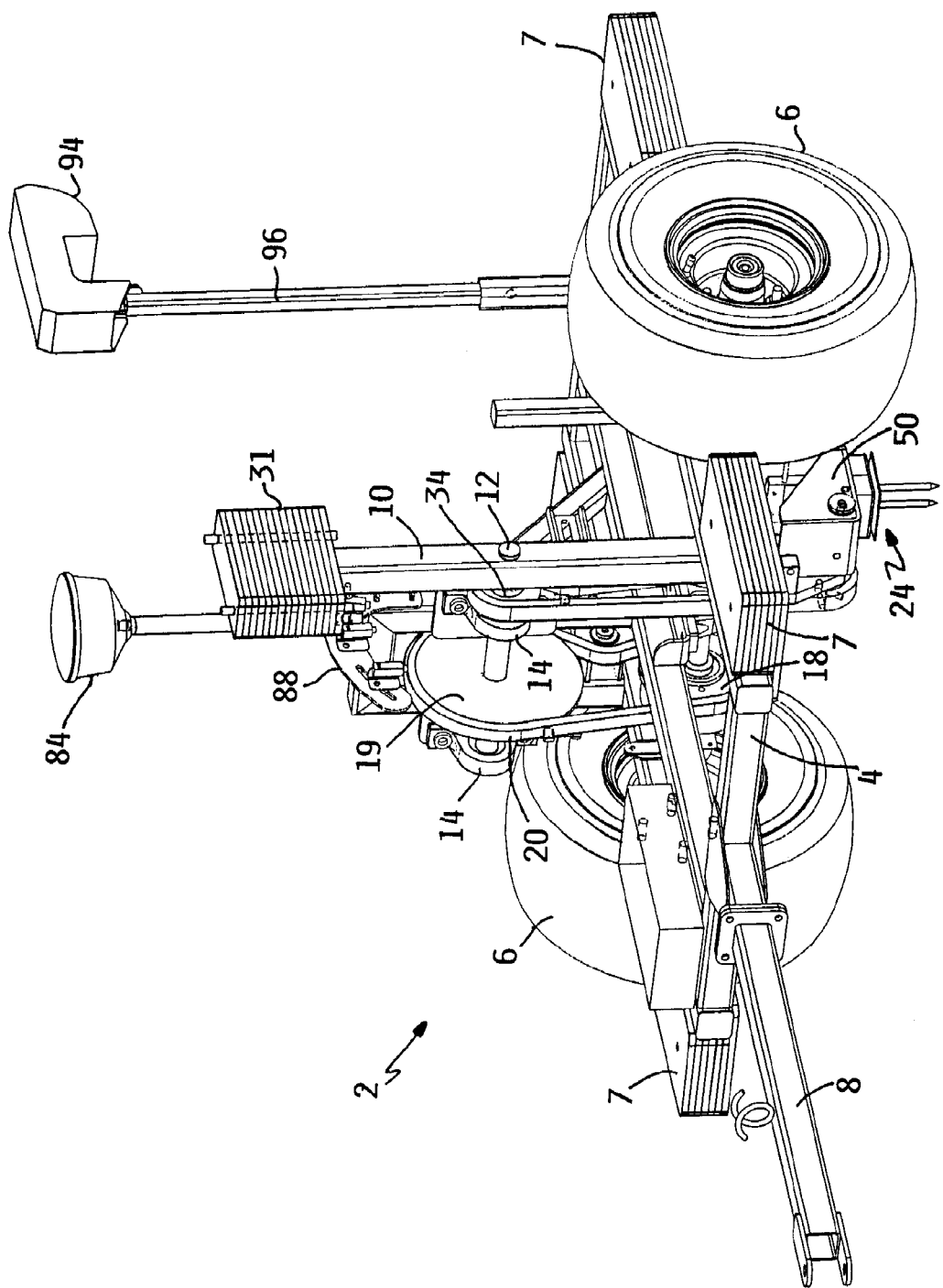
FIG. 2 is a perspective view towards the left front of the mobile turf instrument apparatus of FIG. 1.
Figure 3:
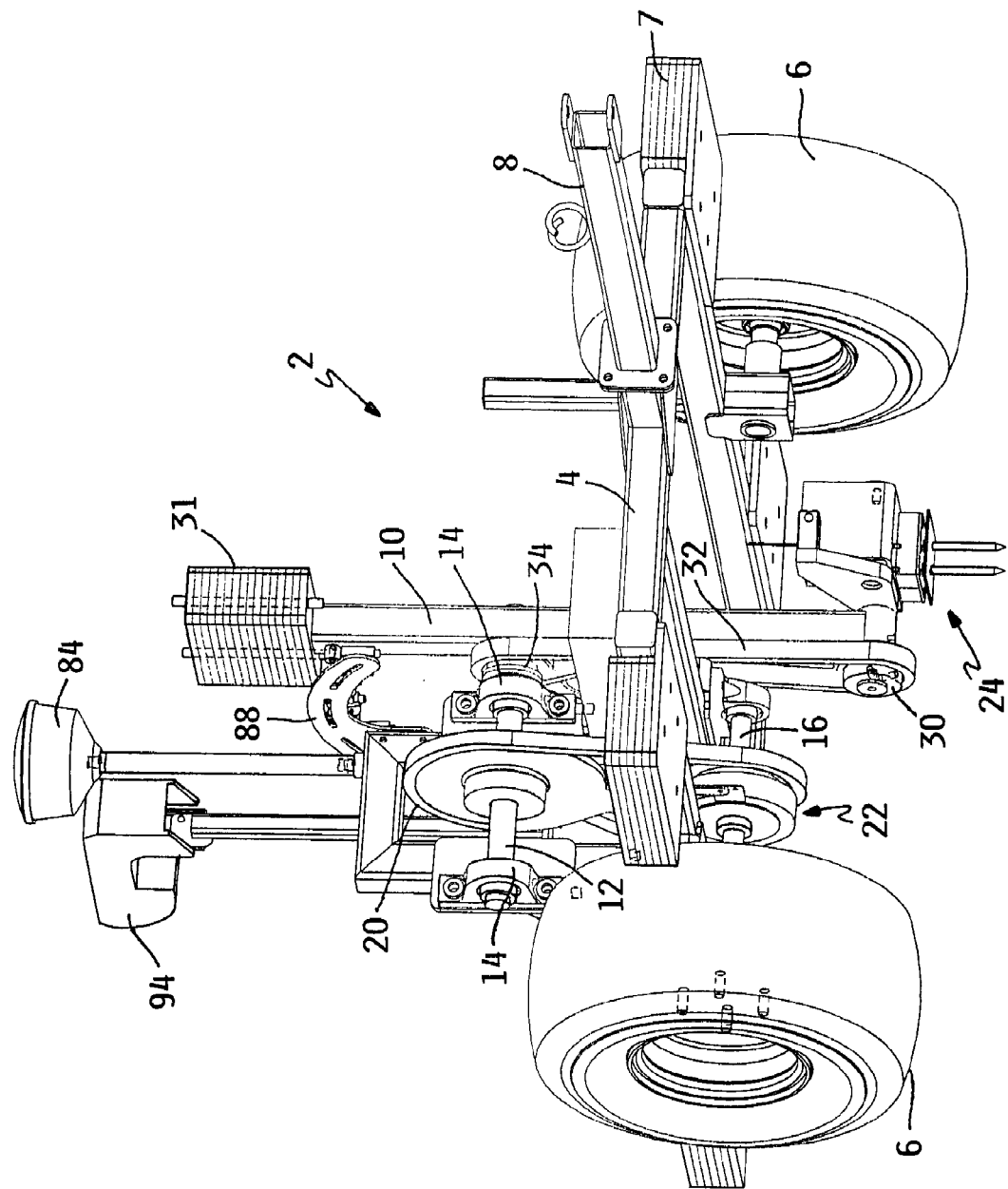
FIG. 3 is a perspective view towards the right front of the mobile turf instrument apparatus of FIG. 1.

FIGS. 1-3 illustrate one embodiment of a mobile turf instrument apparatus 2 according to this invention. Apparatus 2 comprises a mobile platform or frame 4 supported for rolling over the ground by one or more rotatable ground engaging members, such as by a pair of wheels 6. Frame 4 preferably comprises a tow frame having a forwardly extending tongue 8 for allowing frame 4 to be hitched to a motive device in the form of a towing vehicle, such as a mower, utility vehicle, or the like. Alternatively, frame 4 could be pushed by the separate vehicle rather than being towed. Moreover, frame 4 could be self-propelled with the motive device comprising an engine or motor carried on frame 4. Counterweights 7 can be placed on frame 4, preferably at the corners thereof, to add enough weight to frame 4 to prevent frame 4 from bouncing up and down as it is moved over the ground.

Apparatus 2 includes a revolving support in the form of an elongated revolving arm 10. Arm 10 is fixed to an inner end of a substantially horizontal shaft 12 so as to rotate with shaft 12. Shaft 12 extends to one side of frame 4 such that an outer end of shaft 12 is located along one side of frame 4. See FIG. 3. Shaft 12 is rotatably journalled on frame 4 by a pair of spaced bearings 14 carried on frame 4.

Arm 10 is positioned in an open central space in frame 4. In addition, bearings 14 are located high enough on frame 4 such that arm 10 can revolve around the axis of shaft 12 and will clear the ground when doing so. The open central space of frame 4 is also large enough in a fore-and-aft direction to accommodate the revolving motion of arm 10 without arm 10 hitting any part of frame 4.

Arm 10 is revolved by a drive taken from one wheel 6 of frame 4. The stub axle 16 that mounts such wheel 6 is long enough such that the inner end of stub axle 16 is located beneath frame 4 generally parallel to and below shaft 12. See FIG. 3. A first small drive sprocket 18 is carried around stub axle 16 and shaft 12 carries a second larger driven sprocket 19, the two sprockets 18, 19 being connected together by a chain 20. Sprockets 18, 19 are sized to provide a speed reduction between the rotational speed of wheels 6 and that of arm 10.

An electric clutch 22 is also carried on stub axle 16 to selectively drive stub axle sprocket 18. In other words, stub axle sprocket 18 is coupled to stub axle 16 and is rotated by stub axle 16 when clutch 22 is engaged. Conversely, stub axle sprocket 18 is uncoupled from stub axle 16 and is not being rotated by stub axle 16 when clutch 22 is disengaged.

Figure 5:
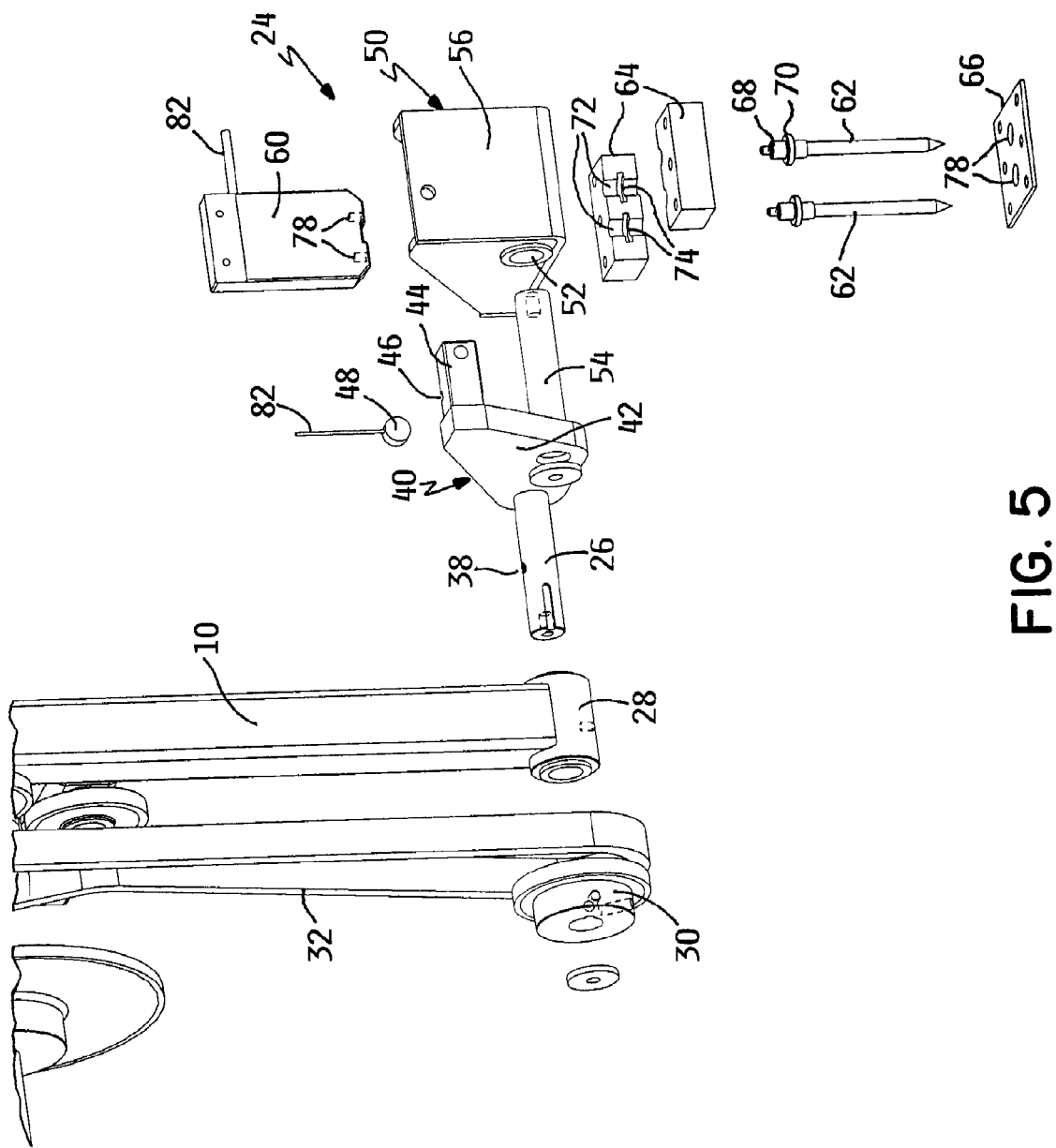
FIG. 5 is an exploded perspective view of the probe assembly of FIG. 4.

Referring now to FIG. 5, a probe assembly indicated generally as 24 is rotatably mounted on one end of arm 10. A pivot shaft 26 on probe assembly 24 extends through a bearing in a hub 28 on the end of arm 10. Pivot shaft 26 is non-rotatably keyed or splined to a small sprocket 30 that is also carried on the end of arm 10. Rotation of probe assembly sprocket 30 relative to the end of arm 10 will also rotate probe assembly 24 relative to the end of arm 10.

The opposite end of arm 10 carries a weight 31. Weight 31 is heavier than the collective weight of probe assembly 24 and sprocket 30 on the other end of arm 10. Thus, when apparatus 2 is stationary and arm 10 is not being revolved by rotation of wheel 6, arm 10 will have a resting position in which weight 31 is lowermost and probe assembly 24 is uppermost, i.e. arm 10 will be vertical and the end of arm 10 carrying weight 31 will be the lower end of arm 10 and the end of arm 10 carrying probe assembly 24 will be the upper end of arm 10. This resting position of arm 10 is not illustrated in the drawings.

Figure 6:
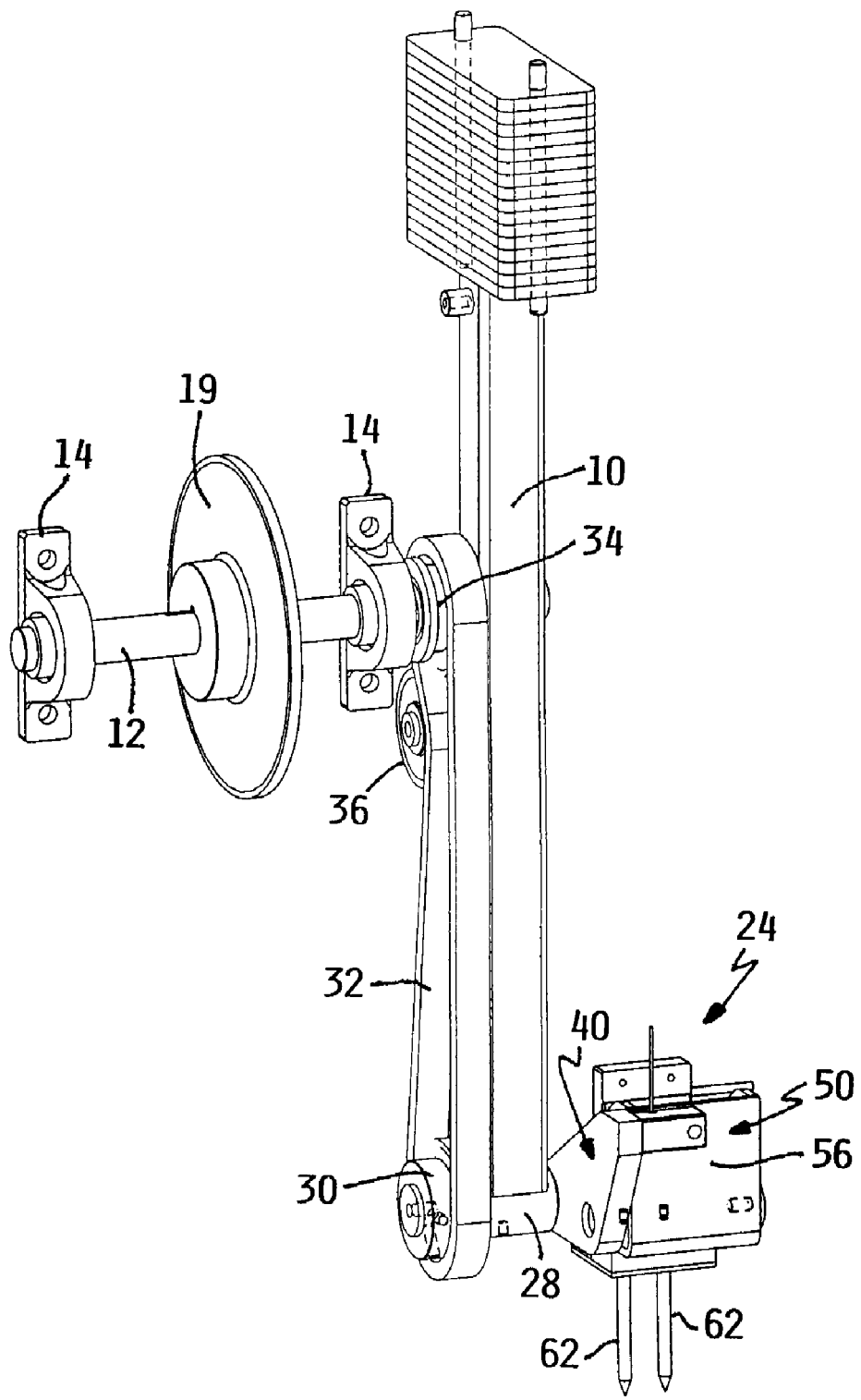
FIG. 6 is a perspective view of the revolving arm that periodically inserts the probe assembly of FIG. 4 into the soil.

Probe assembly sprocket 30 on the end of arm 10 is coupled by a chain 32 to a fixed sprocket 34 that is carried concentrically around horizontal shaft 12 that rotates arm 10. Fixed sprocket 34 is so named because no rotation of sprocket 34 is allowed relative to frame 4. Fixed sprocket 34 is physically clamped or held relative to frame 4 so that it does not rotate. A rotatable idler sprocket 36 is mounted by a bracket 37 on arm 10 substantially immediately beneath fixed sprocket 34. See FIGS. 1 and 6. Idler sprocket 36 helps maintain proper tension on chain 32 during rotation of arm 10.

As arm 10 rotates around horizontal shaft 12 in a given direction, chain 32 produces an equal and opposite counter-rotation of probe assembly sprocket 30 so that probe assembly 24 always remains substantially horizontal relative to frame 4 or to the ground during rotation of arm 10. In other words, a reference mark 38 on the top of probe assembly pivot shaft 26 (shown in FIG. 5) will always remain on the top of shaft 26 whether arm 10 is pointing straight up, straight down, forwards, backwards, or in any direction in between. Thus, probe assembly 24 is self-leveling relative to arm 10 as arm 10 rotates or revolves around the axis of shaft 12.

In a complete revolution of arm 10, chain 32 translates or moves along arm 10 by a distance equal to the number of teeth in fixed sprocket 34 and probe assembly sprocket 30. Fixed sprocket 34 and probe assembly sprocket 30 are identical in size with the same number of teeth. While fixed sprocket 34 does not rotate relative to frame 4 or relative to the ground, fixed sprocket 34 does rotate relative to arm 10 as arm 10 revolves around the axis of shaft 12. One must remember that fixed sprocket 34 is concentrically positioned around shaft 12 to be on the same axis as shaft 12, but fixed sprocket 34 is not rotatably coupled to shaft 12 and is not part of arm 10. Thus, the rotation of arm 10 does produce relative rotation between arm 10 and fixed sprocket 34.

Probe assembly 24 comprises two parts that are further mounted for pivoting relative to one another during operation of probe assembly 24. These two parts comprise an L-shaped bracket 40 having a side wall 42 and a top rail 44 arranged at a perpendicular angle relative to side wall 42. See FIG. 5. Pivot shaft 26 that mounts probe assembly 24 for pivoting on arm 10 is connected to an inner face of side wall 42 of bracket 40. Top rail 44 of bracket 40 includes a recess, slot or cavity 46 for holding a load cell 48, e.g. an Omega Engineering LC302-500 load cell.

The other part of probe assembly 24 comprises a box-shaped housing 50 with an open top. Housing 50 includes a bore 52 for receiving a pivot pin 54 carried on the outer face of side wall 42 of bracket 40, i.e. on the face of side wall 42 that is opposite to the face that carries pivot shaft 26. Pivot pin 54 allows housing 50 to rock back and forth relative to bracket 40.

Figure 4:
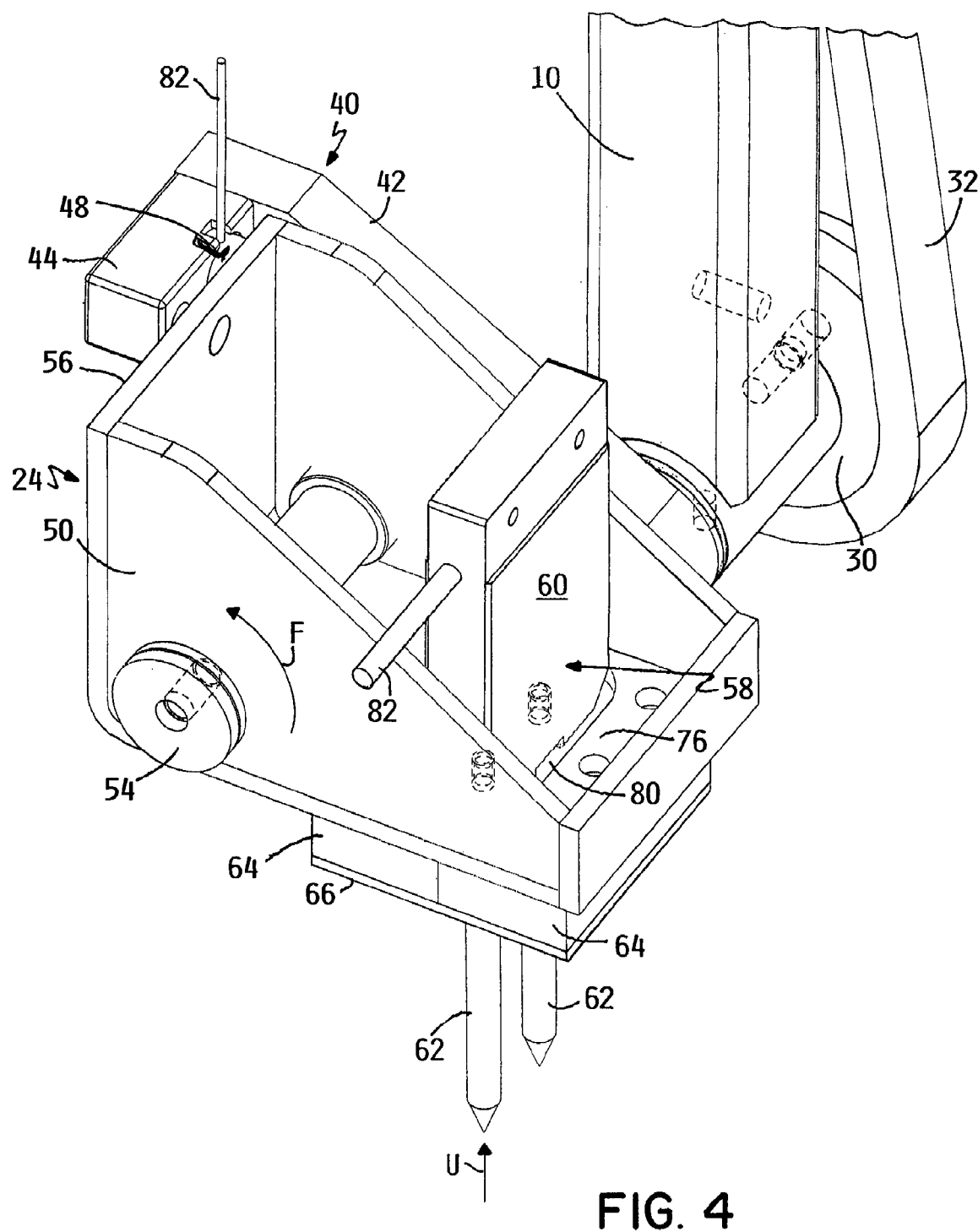
FIG. 4 is a perspective view of the probe assembly of the mobile turf instrument apparatus of FIG. 1.

Referring to FIG. 4, when bracket 40 and housing 50 are assembled together, top rail 44 of bracket 40 is juxtaposed substantially immediately ahead of a front wall 56 of housing 50. Thus, load cell 48 that is held on top rail 44 is positioned to abut with or be closely spaced from front wall 56 of housing 50. As probe assembly 24 is pushed into the ground, rocking of housing 50 about pivot pin 54, depicted by the arrow F in FIG. 4, will vary the force exerted on load cell 48 by housing 50.

A Timed Domain Reflectometer (TDR) soil moisture sensor package 58, e.g. a Campbell Scientific CS620, is carried by housing 50 of probe assembly 24. Sensor package 58 includes a sensor body 60, a pair of ground penetrating probes 62, a pair of probe mounting blocks 64, and a clamping plate 66. Each probe 62 includes a mounting collar 68 around the upper end of probe 62 with the upper end of probe 62 sticking upwardly out of mounting collar 68. Each mounting collar 68 includes an annular, radially extending mounting flange 70. Probes 62 are metallic and mounting collars 68 may be made from any suitably strong and durable material, such as a composite material.

Mounting blocks 64 are provided as a separate pair of blocks 64 to allow blocks 64 to be separated for installation of probes 62. Each mounting block 64 includes a pair of semi-circular grooves 72 with a horizontal channel 74. Each groove 72 is sized to conform to the outer diameter of mounting collar 68 on the upper end of probe 62. Each channel 74 is sized to receive a mounting flange 70 on collar 68. Each mounting block 64 is made of an electrically non-conductive material, such as ABS plastic.

Mounting collars 68 of probes 62 are placed into grooves 72 and channels 74 of one mounting block 64. Then, the other mounting block 64 is superimposed over probes 62 and abutted with the first mounting block 64 to clamp probes 62 between the two mounting blocks 64. Clamping plate 66 is then bolted or screwed to housing 50 to clamp both mounting blocks 64 to the underside of the floor 76 of housing 50. When so mounted, probes 62 will extend downwardly away from housing 50 through openings 78 in clamping plate 66 that are large enough to receive probes 62.

The upper ends of probes 62 project upwardly far enough to reach sensor body 60. Sensor body 60 is positioned or held within housing 50 of probe assembly 24. Sensor body 60 is provided with a pair of threaded probe connections 78 on the bottom of sensor body 60 for receiving the upper threaded ends of probes 62 to establish both a mechanical and electrical connection to probes 62. See FIG. 5. Sensor body 60 can reach the upper ends of probes 62 through a slot 80 provided in floor 76 of housing 50. Thus, effectively sensor body 60 is carried on the upper ends of probes 62 with the upper ends of probes 62 sticking up into probe connections 78 on sensor body 60. Probes 62 are preferably first inserted through slot 80 and screwed into sensor body 60 while sensor body 60 sits in housing 50 and then mounting blocks 64 are abutted around probes 62 beneath housing 50 with clamping plate 66 finally being bolted to housing 50 to hold everything in place.

The upward force exerted on probes 62 as they are inserted into the ground, represented by the arrow U in FIG. 4, is transmitted through mounting collars 68 and mounting blocks 64 to the underside of housing 50. Thus, damage to sensor body 60 from the force U generated during probe insertion is either eliminated or greatly reduced. Mounting collars 68, mounting blocks 64, and how mounting blocks 64 are abutted and bolted to housing 50 are a simple and durable mounting system for probes 62 and sensor body 60.

It should be clear that both load cell 48 and sensor body 60 are electrically connected to various control and measurement electronics located elsewhere. These electrical connections are diagrammatically illustrated by electrical wires 82. Thus, the readings that are derived from load cell 48 and sensor package 58 can be logged or recorded in any appropriate device, such as a data logger or computer (not shown). The computer may be carried on frame 4 itself, or on the vehicle used to tow the frame 4, and may be hardwired to load cell 48 and sensor body 60 as suggested by wires 82. Alternatively, wireless communication could be established between load cell 48 and sensor body 60 to allow the readings to be wirelessly communicated to the computer.

As frame 4 moves across the turf, and when clutch 22 is engaged, arm 10 will rotate or revolve from the drive taken from wheel 6. As arm 10 revolves, probe assembly 24 rotates correspondingly in a way that maintains probe assembly 24 in a horizontal position with probes 62 facing the ground. At some point, arm 10 will approach the ground and probes 62 will be pushed into the ground.

Clutch 22 can be disengaged to uncouple arm 10 from the drive from wheel 6 from some time shortly before probes 62 have entered the ground (assuming arm 10 has sufficient momentum) to some time shortly after probes 62 have entered the ground. If clutch 22 is disengaged shortly before probes 62 have entered the ground and the speed of the arm is high enough, then the momentum of arm 10 will be sufficient to cause arm 10 to continue to rotate and to insert probes 62 in the ground. Once probes 62 are inserted into the ground, then arm 10 will still continue to rotate since probes 62 are now stuck in the ground but frame 4 is continuing its forward motion. Thus, when the drive is actually disconnected from arm 10 from a moment just prior to or just after probe insertion and/or during the entire time probes 62 are in the ground, arm 10 will to the naked eye look like it is revolving as before.

There are two reasons for disconnecting the drive to arm 10 while probes 62 are inserted into the ground. One is to avoid having probes 62 make elongated holes or slots in the ground. The other is to avoid putting too much torque or stress on probes 62 or on the other components of sensor package 58 while probes 62 are in the ground. This will further help avoid damaging probes 62 or the other components of sensor package 58.

In any event, the drive disconnection to arm 10 lasts only so long as probes 62 are in the ground. When arm 10 swings around past bottom dead center and probe assembly 24 is about to begin to lift probes 62 out of the ground, clutch 22 is reengaged. This couples arm 10 to the drive from wheel 6 to continue the rotation of arm 10 again.

When probes 62 of probe assembly 24 are in the ground, electrical energy can be supplied to probes 62 from the control electronics to initiate a soil moisture measurement. This measurement will then be reported back to the computer as described above and will be recorded. A GPS device 84 or other global locating device can be carried on frame 4. Thus, the reported soil moisture reading can be correlated to the location where the reading was taken.

This is also true of the readings of any other turf parameters that will be taken and recorded. Such readings will similarly be correlated to the GPS location of frame 4 at the time they are taken. Thus, an accurate map can be made of the turf area over which frame 4 is moved which map will display the various readings of the measured turf parameters and where such readings occurred.

Load cell 48 positioned between housing 50 and bracket 40 of probe assembly 24 is used to measure soil compaction when probes 62 are being inserted in the ground. This is so because the force exerted on load cell 48 by housing 50 will vary depending upon the hardness of the ground. The rocking action of housing 50 determines the force on load cell 48 and the rocking action varies depending upon the hardness of the ground. Housing 50 will rock more during probe insertion when the ground is hard as opposed to when the ground is soft. Thus, a measurement of soil compaction can be taken and recorded along with the soil moisture reading. Thus, the same probe assembly 24 does double duty since it functions both as part of a penetrometer used to measure soil compaction as well as part of a soil moisture sensor.

Figure 7:
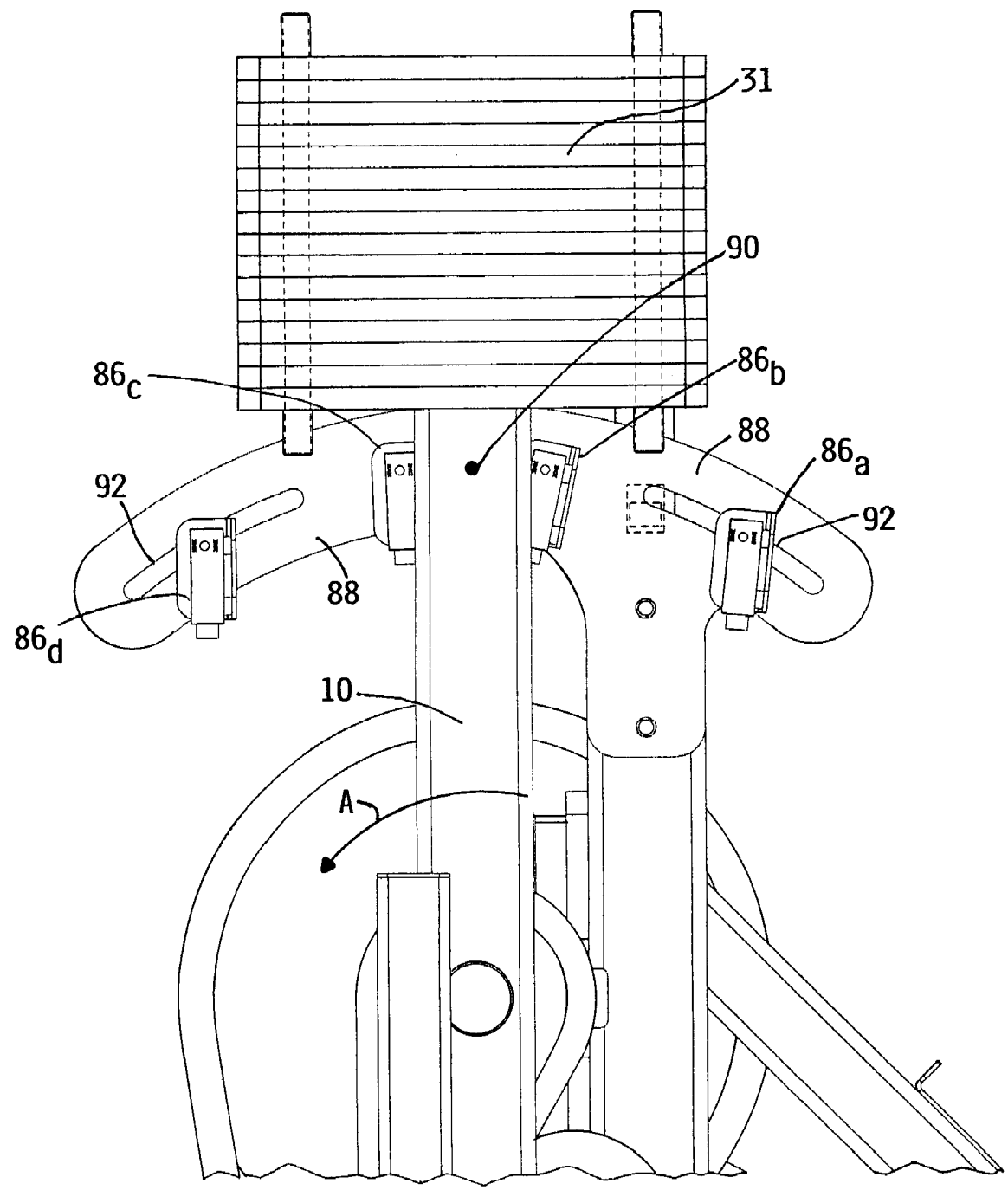
FIG. 7 is a side elevational view of the controls that engage and disengage the drive to the revolving arm of FIG. 6 and that start and stop the taking of readings from various turf measurement instruments carried on the arm.

Referring now to FIG. 7, a plurality of limit switch controls 86 are mounted in a fixed position on frame 4 along an arcuate flange 88. Flange 88 is positioned symmetrically relative to the top dead center position of arm 10 as shown in FIG. 7. Each limit switch 86 senses or is triggered by a magnetic or other trigger 90 carried on arm 10. Thus, as arm 10 revolves in the direction of rotation indicated by the arrow A in FIG. 7, limit switches 86 will be selectively closed in sequence beginning with the first limit switch 86a and ending with the fourth limit switch 86d.

The first and fourth limit switches 86a and 86d control the engagement and disengagement of clutch 22 respectively. In other words, when the first limit switch 86a is tripped shortly after probe assembly 24 enters the ground, clutch 22 will be disengaged. As the fourth limit switch 86d is tripped as probe assembly 24 just begins to lift out of the ground, clutch 22 will be engaged. The precise positioning of the first and fourth limit switches 86a and 86d can be adjusted by sliding them back and forth in arcuate slots 92 carried on flange 88. This allows the user to adjust the disengagement of clutch 22 to correspond to when probes 62 have just been inserted into the ground and to adjust the engagement of clutch 22 to when probes 62 are just about to lift out of the ground.

The second and third limit switches 86b and 86c signal to the control electronics when to start and stop the soil moisture and soil compaction sensing. Sensing starts when second limit switch 86b is tripped. Sensing stops when third limit switch 86c is tripped. The second and third limit switches 86b and 86c could be replaced, however, with a time delay following tripping of first limit switch a. In other words, sensing could start and stop during a predetermined time interval that begins after a predetermined time delay following the tripping of first limit switch 86a.

In addition to measuring and recording parameters that are derived from the insertion of probe assembly 24 into the ground, frame 4 could carry other turf instruments that do not depend upon such an insertion. For example, a spectrometer 94 for measuring the health of the grass could be mounted on frame 4 at any suitable location, such as on a post 96 on the rear of frame 4. As frame 4 moves over the ground, spectrometer 94 measures the vigor or health of the turf using light reflectance as described in the Background of the Invention section of this application. Such a turf health measurement reading would then be correlated to the GPS location of frame 4 and stored with the soil moisture and soil compaction readings in the overall map of the turf area being surveyed. These turf health measurement readings could be taken at the same time as the soil moisture or compaction readings or at different times.

Apparatus 2 of this invention provides for measuring various parameters of the turf using a probe assembly 24 that is periodically inserted into and removed from the ground. It does so, however, by mounting such a probe assembly on a mobile frame to allow the readings derived from probe assembly 24 to be accomplished automatically and without effort by the operator as frame 4 is driven or otherwise moved over the turf area to be surveyed and measured. This greatly enhances the productivity of the operator. The operator need not walk the turf area by foot and stick a hand held soil moisture sensor into the ground. The vehicle need not be stopped to allow the probe assembly to be inserted into the ground.

In addition, frame 4 can be used to carry other turf measurement instruments, such as spectrometer 94, that measure other turf parameters using methods that do not require physical penetration of the ground or in fact any engagement with the turf or the ground. Thus, apparatus 2 of this invention can provide a whole range of turf parameter measurements and record and map such measurements over the turf area being surveyed. Obviously, sensors other than those described herein for measuring other turf parameters could be added to frame 4 of apparatus 2. For example, instruments for measuring soil salinity or canopy temperature could be added.

While a simple mechanical drive from wheel 6 is preferred for rotating arm 10, arm 10 could be driven by a separate hydraulic or electric motor. Soil moisture sensors other than TDR soil moisture sensors could be used. Thus, this invention is not limited to the specific details of the embodiment disclosed herein.

Figure 11:
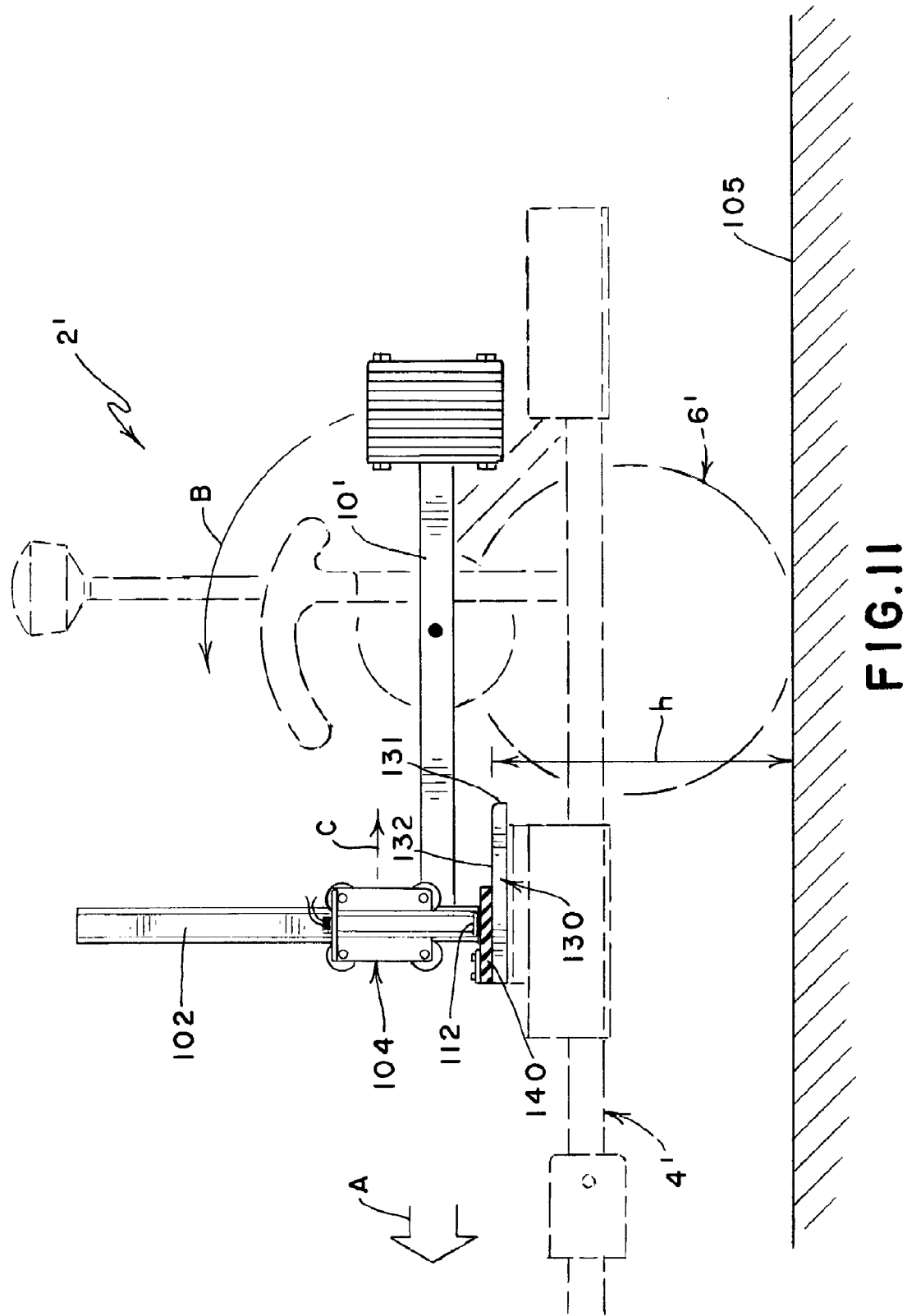
FIG. 11 is a side elevational view of the second embodiment of the mobile turf instrument apparatus according to this invention, particularly illustrating the impact hammer having engaged against a cushioned portion of the stop plate just prior to the elevation of the impact hammer upwardly along the guide.
Figure 12:
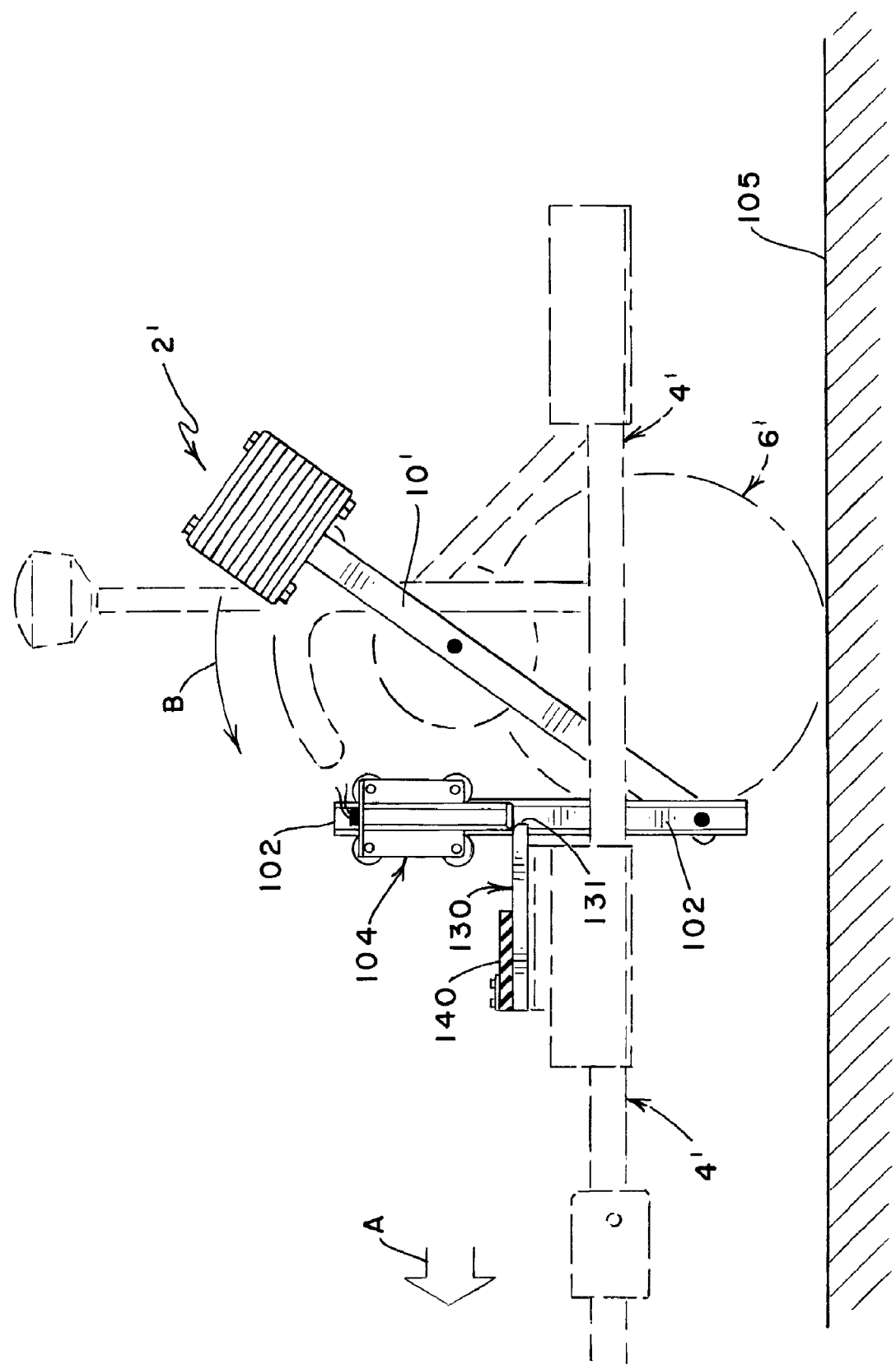
FIG. 12 is a side elevational view similar to FIG. 11, particularly illustrating the impact hammer having moved upwardly along the guide and having translated longitudinally along the length of the stop plate just prior to the impact hammer dropping off the rear edge of the stop plate.
Figure 13:
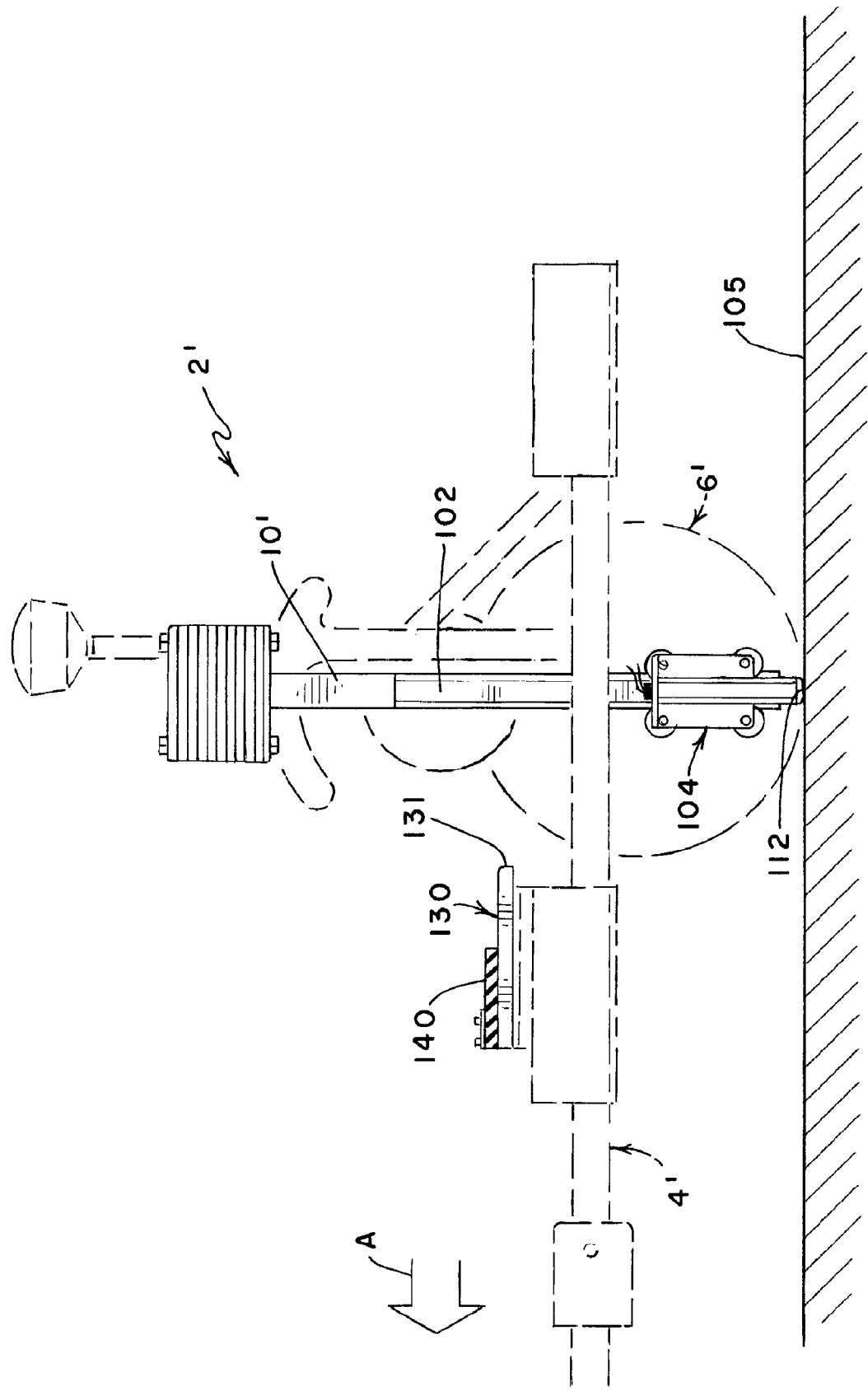
FIG. 13 is a side elevational view similar to FIG. 12, particularly illustrating the impact hammer having dropped off the stop plate and having fallen downwardly back along the length of the guide to impact against the surface being traversed by the apparatus.

A second embodiment of a mobile turf instrument apparatus according to this invention is illustrated in FIGS. 11-13 as 2'. Components of apparatus 2' that are the same as those of apparatus 2 will be referred to by the same reference numerals as used for those components of apparatus 2 but with a prime suffix being added, e.g. frame 4' versus frame 4. Much of apparatus 2' is the same as apparatus 2 including the use of a mobile frame 4' that carries a revolving arm 10'. Thus, only the differences between apparatus 2' and apparatus 2 will be specifically described hereafter.

Figure 8:
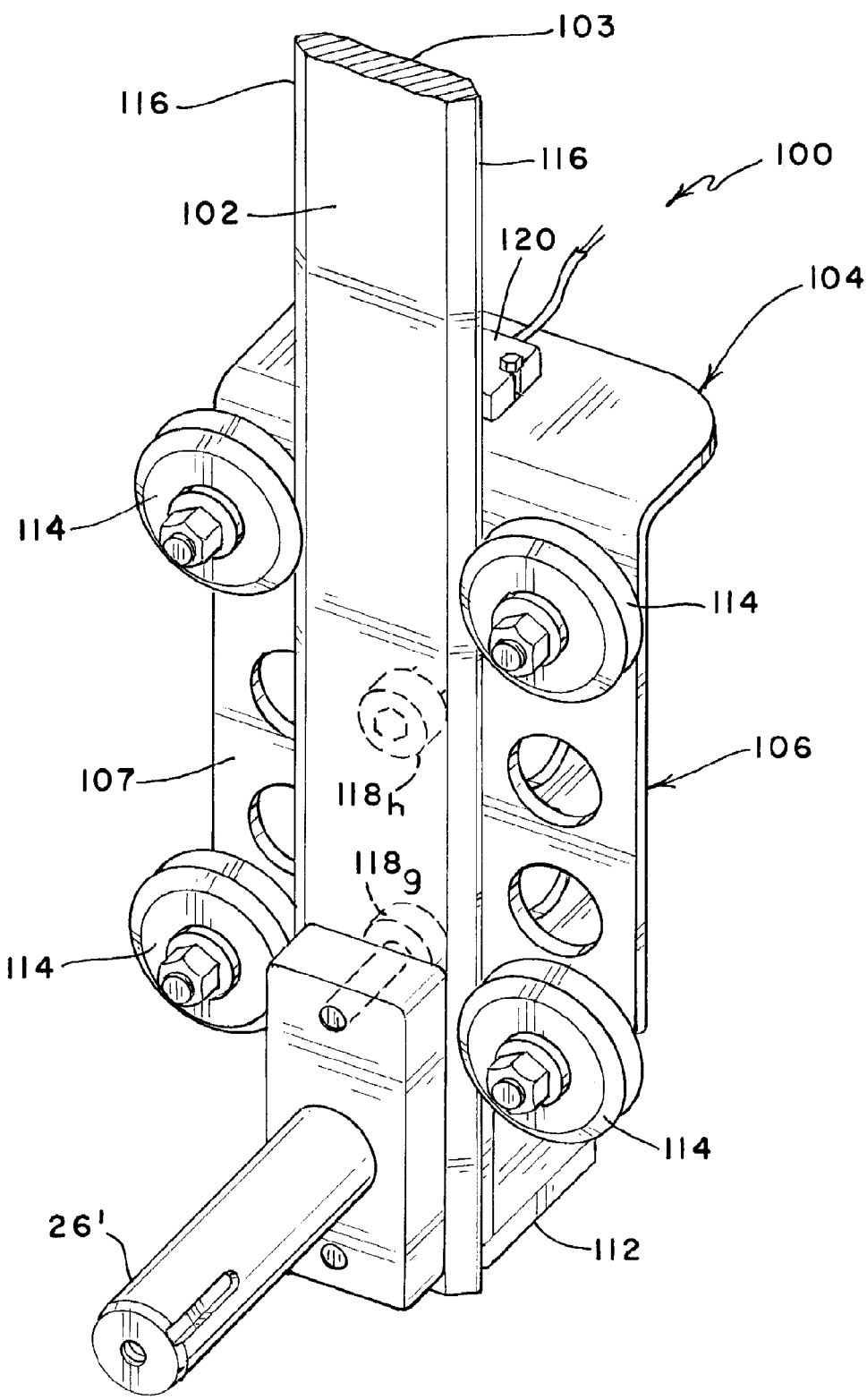
FIG. 8 is a perspective view of a portion of a second embodiment of a mobile turf instrument apparatus according to this invention, particularly illustrating one side of an instrument assembly that is carried on one end of the revolving arm of the apparatus.

The major difference between apparatus 2' and apparatus 2 is the use of a different type of instrument assembly 100 on the end of revolving arm 10'. Referring to FIG. 8, instrument assembly 100 has two major components: an elongated rail or guide 102 that is several feet long and an impact hammer 104 carried on guide 102. Normally, hammer 104 is in a lower position on guide 102 and is being transported by guide 102 in a circular path due to the rotation of revolving arm 10'. However, as will be described in more detail hereafter when the operation of apparatus 2' is set forth, hammer 104 is temporarily uncoupled from the circular path to allow hammer 104 to rise into an upper position on guide 102 and to then suddenly fall under the influence of gravity back down along guide 102 until hammer 104 impacts against the surface 105 over which frame 4' is traveling.

Referring further to FIG. 8, guide 102 has a lower end that mounts a pivot shaft 26' that functions like pivot shaft 26 of apparatus 2 to continually pivot guide 102 relative to revolving arm 10' during the 360° rotation of arm 10' in each cycle of operation of arm 10'. The purpose of this is to keep instrument assembly 100 substantially horizontal and level with guide 102 remaining in a substantially upright, vertical orientation as arm 10' revolves. This is done in the same manner and using the same structure, namely sprocket 30, chain 32, and fixed sprocket 34, as that which keeps probe assembly 24 substantially level as arm 10 revolves. The only difference is that pivot shaft 26' of guide 102 is non-rotatably keyed or splined to sprocket 30 in place of pivot shaft 26 of probe assembly 24.

Hammer 104 comprises a body 106 that includes a vertical pedestal or column 108 formed by a pair of spaced vertical walls 110 that terminate in a bottom or foot 112. See FIG. 9. Foot 112 is the portion of hammer 104 that impacts against surface 105 over which frame 4' is traveling when hammer 104 is dropped. Body 106 also mounts a plurality of rotatable, grooved rollers 114 above foot 112 which engage against tapered, substantially V-shaped side edges 116 of guide 102. One purpose of grooved rollers 114 is to retain hammer 104 on guide 102 after hammer 104 is first installed thereon by placing hammer 104 above the top end of guide 102, by aligning rollers 114 with the top end of side edges 116, and by then dropping hammer 104 down along guide 102 with side edges 116 being received in the grooves in rollers 114. Another purpose of grooved rollers 114 is to provide a low friction, smooth sliding engagement with guide 102.

Referring again to FIG. 8, the usual or normal lower position of hammer 104 on guide 102 is established by two vertically abutting spacers 118 located in the space or gap between one side 103 of guide 102 and the adjacent face 107 of body 106 of guide 102. There is a lower spacer 118g carried on guide 102 extending towards face 107 of body 106 of hammer 104 and an upper spacer 118h carried on hammer 104 extending towards side 103 of guide 102. When hammer 104 is in its usual or normal lower position, upper spacer 118h abuts against and rests atop lower spacer 118g to prevent hammer 104 from falling downwardly off guide 102. During approximately 270° of each 360° revolution of revolving arm 10', spacers 118 are in their abutting, engaged position with hammer 104 remaining in its lower position at the bottom end of guide 102. Spacers 118 are not shown in FIG. 8 in their abutting engagement because hammer 104 is shown in FIG. 8 in a position relative to guide 102 that is slightly elevated from its usual or normal lower position on guide 102.

Hammer 104 carries an accelerometer 120 that is used to measure the deceleration of hammer 104 when hammer 104 impacts against surface 105 over which frame 4' is traveling. When that surface 105 is a turf, soil or ground surface, such deceleration readings correlate with the compaction or hardness of surface 105 and provide useful information in this regard. For example, the readings provided by accelerometer 120 may be correlated with the GPS position of the vehicle to provide a compaction map of the entire area traversed by frame 4', indicating which areas are too compacted, which areas are properly compacted, and which areas may be too loosely compacted, thereby allowing appropriate corrective action to be taken. This general type of accelerometer equipped hammer is known in the sports field and golf course art as a Clegg type soil impact tester.

Figure 9:
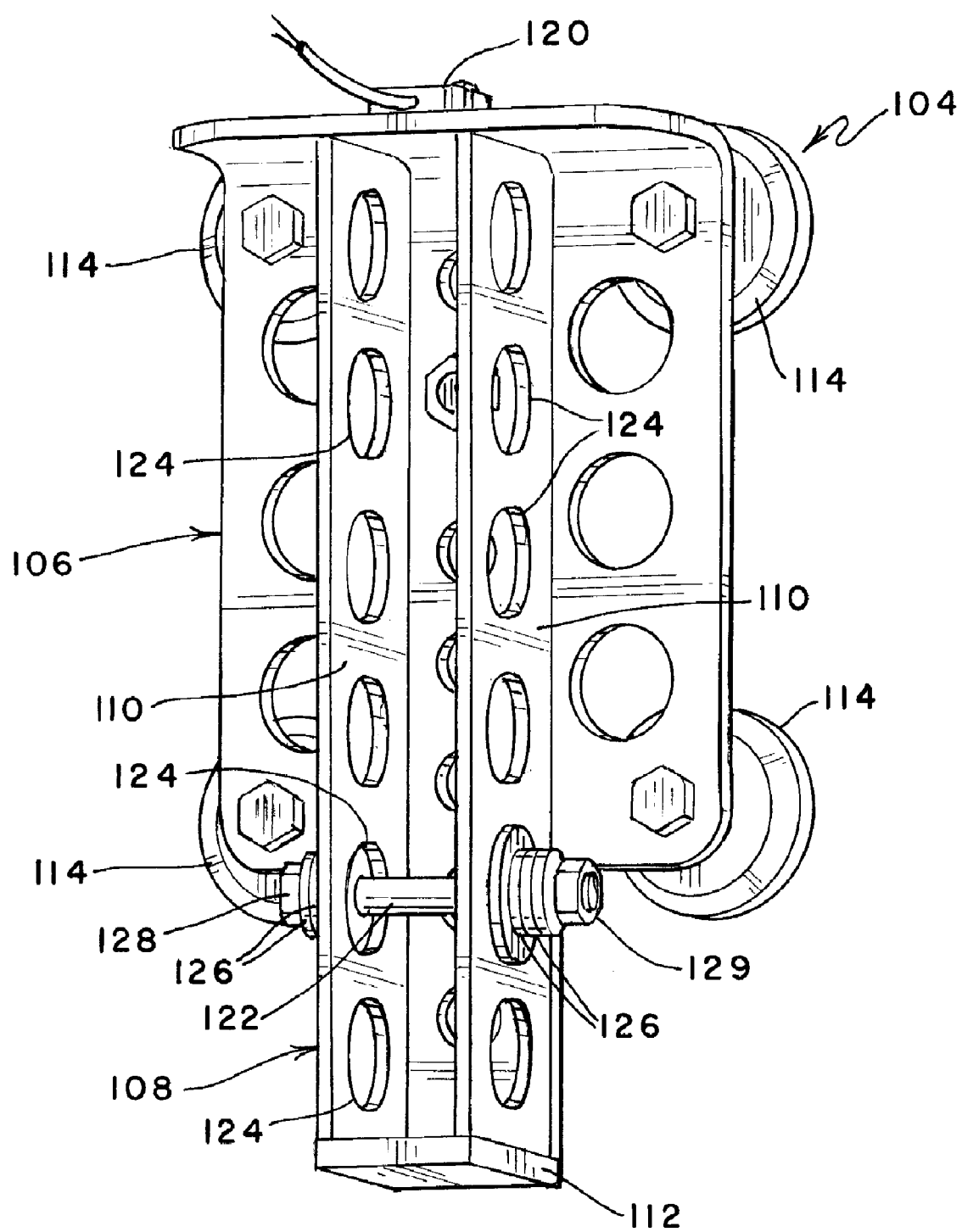
FIG. 9 is a perspective view similar to FIG. 8, but illustrating the opposite side of a portion of the instrument assembly shown in FIG. 8, namely the opposite side of the accelerometer equipped impact hammer.

In performing the measuring function described above, it is customary that hammer 104 have a predetermined weight and be dropped from a predetermined height above surface 105. It would be possible to form or build hammer 104 out of materials that provide precisely the correct predetermined weight, but this would require strict manufacturing tolerances. Instead, as best shown in FIG. 9, hammer 104 can be conveniently provided with a weight adjustment device comprising a bolt or pin 122 that extends through a pair of aligned horizontal holes 124 in the vertical walls 110 of hammer 104. Various washers 126 can be added to either end of pin 122 and can be clamped against walls 110 by the head 128 of bolt or pin 122 and by a nut 129 to allow the weight of hammer 104 to be fine tuned to provide the correct predetermined weight for hammer 104.

Figure 10:
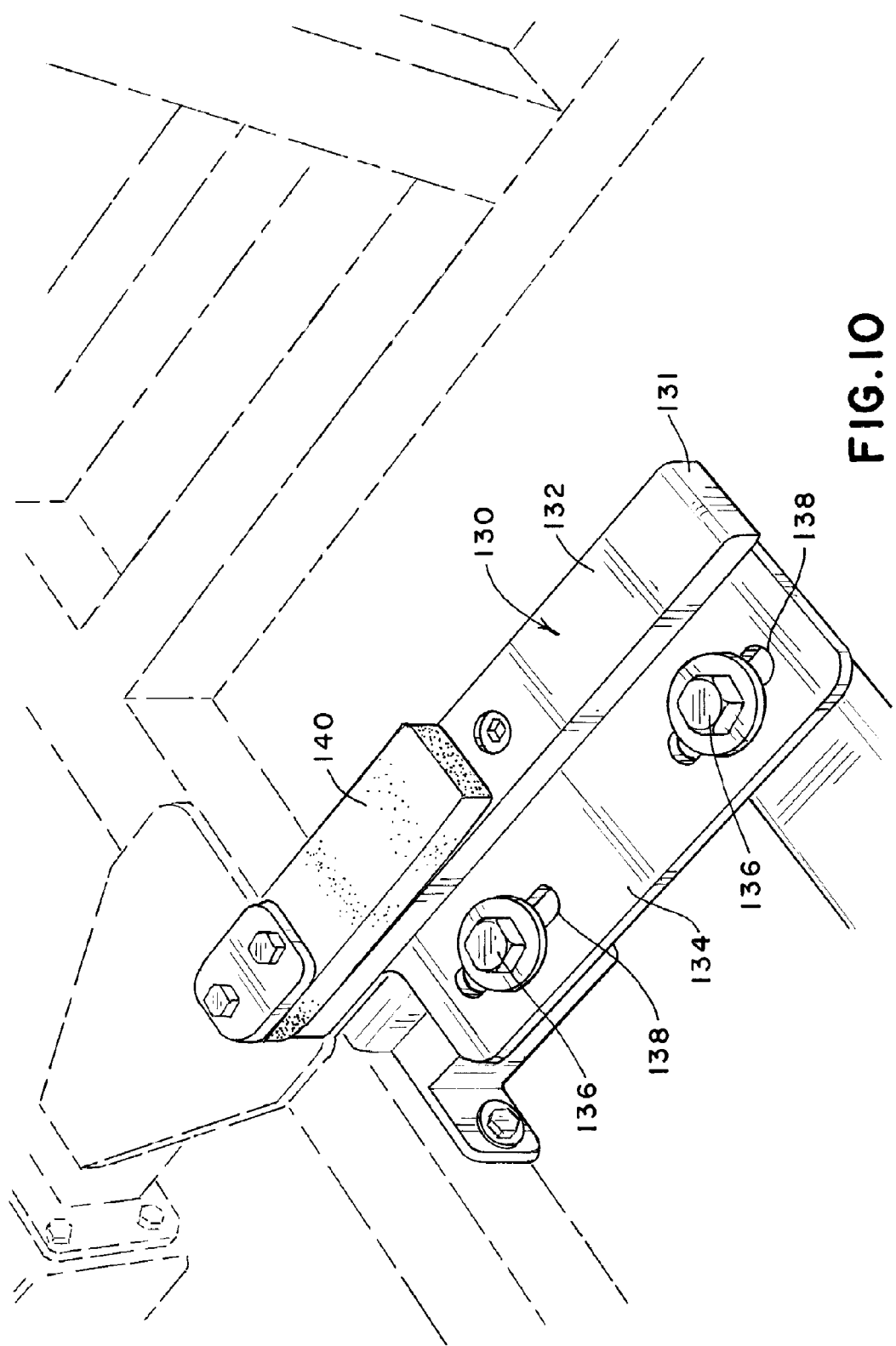
FIG. 10 is a perspective view of another portion of the second embodiment of the mobile turf instrument apparatus according to this invention, particularly illustrating a stop plate carried on the mobile frame of the apparatus with the stop plate serving to temporarily vertically uncouple the impact hammer from a vertical guide of the instrument assembly to permit the hammer to slide or ride up the guide.

Referring now to FIG. 10, establishing the predetermined height from which hammer 104 is dropped is accomplished by adding a substantially horizontal stop defined by a stop plate 130 to frame 4' of apparatus 2'. Stop plate 130 has an upper surface 132 that is located above the plane on which the wheels 6' of frame 4' roll, i.e. above the nominal plane of surface 105 excluding local variations in the contour of surface 105, by a height h that is equal to the correct predetermined drop height for hammer 104. Height h is depicted in FIG. 11. Stop plate 130 is oriented to be parallel to a longitudinal, forward direction of motion of frame 4' which direction of motion is indicated by the arrow A in FIGS. 11-13. In addition, stop plate 130 is laterally positioned on frame 4' such that hammer 104 will hit stop plate 130 during a portion of each revolution of revolving arm 10', but guide 102 and arm 10' will miss stop plate 130 passing down past the side of stop plate 130 even as hammer 104 hits stop plate 130.

Stop plate 130 is bolted to or otherwise carried on a mount 134 that fixedly attaches stop plate 130 to frame 4' when mounting bolts 136 are tightened relative to frame 4'. Mount 134 includes elongated longitudinal slots 138 through which mounting bolts 136 pass to provide mount 134, and thus to provide stop plate 130, with limited adjustability in a longitudinal or fore-and-aft direction for a purpose to be described hereafter. In addition, the front end of stop plate 130 has a relatively soft or compressible landing pad or cushion 140 on which hammer 104 lands when hammer 104 first contacts stop plate 130. Cushion 140 can be made of rubber though other materials may also be used. The purpose of cushion 140 is to prevent any damage to hammer 104 when hammer 104 first engages stop plate 130 and to lessen the noise created by such engagement.

The operation of apparatus 2' will now be described with reference to FIGS. 11-13. As frame 4' moves over surface 105, arm 10' revolves in continuously repeating cycles of rotation, making successive 360° revolutions one after another. The operation of instrument assembly 102 in a single such revolution of arm 10' will be described. However, it must be understood that this operation is repeated in each revolution of arm 10'.

Normally, for most of each revolution of arm 10', hammer 104 is carried in a circular path by arm 10' with hammer 104 being retained in its lower position on guide 102 by the stop or limit provided by the abutting engagement of spacers 118. The direction of rotation of arm 10' is indicated by the arrow B in FIG. 11. As shown in FIG. 11, at some point in the rotation of arm 10' during each revolution, foot 112 of hammer 104 will land against rubber cushion 140 on stop plate 130. This is the moment in time shown in FIG. 11.

As arm 10' continues its rotation, hammer 104 is still tied to guide 102 in a longitudinal or fore-and-aft sense but is now freed or uncoupled from guide 102 in a vertical sense. Thus, guide 102 will cause hammer 104 to begin to slide rearwardly along stop plate 130 towards a rear edge 131 of stop plate 130 as indicated by the arrow C in FIG. 11. During this rearward motion along stop plate 130, hammer 104 will first drop off rubber cushion 140 and down onto upper surface 132 of stop plate 130. Eventually, hammer 104 will reach rear edge 131 of stop plate 130.

During the rearward motion of hammer 104 along the length of stop plate 130, hammer 104 has risen up or been elevated along much of the length of guide 102 with hammer 104 eventually reaching its upper position on guide 102 when hammer 104 reaches rear edge 131 of stop plate. This is the moment in time shown in FIG. 12. The elevation of hammer 104 along guide 102 occurs simply because hammer 104 is prevented from moving downwardly by stop plate 130 while guide 102 misses stop plate 130 and continues downwardly in its travel due to the rotation of arm 10'.

Once hammer 104 reaches rear edge 131 of stop plate 130 as shown in FIG. 12, the next increment of rotation of arm 10' will cause hammer 104 to be pushed past rear edge 131 of stop plate 130. Once this happens, the force of gravity will take over and hammer 104 will fall under the influence of gravity back down along the length of guide 102. Eventually, foot 112 of hammer 104 will impact against surface 105. This is the moment in time shown in FIG. 13. During this impact, readings can be taken from accelerometer 120 to indicate the compaction or hardness of surface 105 at the spot which was just impacted by hammer 104.

Desirably, frame 4' is propelled forwardly by the operator at a predetermined forward reference speed and the various parts of apparatus 2' are dimensioned so that the moment of impact of hammer 104 occurs at the bottom dead center position of arm 10' as shown in FIG. 13. The moment of impact also occurs prior to spacers 118 reengaging with one another. In other words, foot 112 of hammer 104 impacts against surface 105 while spacers 118 are still slightly vertically spaced apart from one another similar to the spacing that is shown in FIG. 8. The free fall of hammer 104 back down along guide 102 must not be interrupted or cut short by untimely engagement of spacers 118 since the drop of a hammer of a predetermined weight from a predetermined height until impact with the ground is part of the measurement standards established for Clegg type soil impact testers.

With the moment of hammer impact occurring at the bottom dead center position of arm 10' as shown in FIG. 13, hammer 104 has substantially no or zero net longitudinal speed relative to surface 105. In other words, the forward speed of frame 4' has been substantially offset or canceled out by the rearward speed of arm 10' when arm 10' is at bottom dead center, assuming that the speed of frame 4' is being correctly maintained by the operator at the reference speed.

The longitudinal fore and aft adjustability of stop plate 130 is provided to compensate for any friction losses that might occur between hammer 104 and guide 102. For example, when the operator propels frame 4' forwardly at the correct reference speed, friction losses might delay the moment of hammer impact until arm 10' has moved past bottom dead center. Accordingly, slots 138 in mount 134 of stop plate 130 allow stop plate 130 to be moved forwardly as far as need be to compensate for that. This fine tuning in the longitudinal fore and aft location of stop plate 130 would be done on a trial and error basis until hammer 104 consistently impacts against surface 105 at the bottom dead center position of arm 10' when frame 4' is being propelled at the correct reference speed.

Instrument assembly 100 of apparatus 2' operates to measure surface compaction or hardness merely through impact of hammer 104 with surface 105 without requiring the insertion of anything into surface 105. Thus, while instrument assembly 100 can be used on any type of surface, it is particularly useful for operation on artificial turf surfaces of the type increasingly being used on sports fields. Recent artificial turf surfaces comprise a backing material that is laid atop the ground with the backing material having upstanding ribbons of artificial fibers that resemble blades of grass. In addition, such artificial turf surfaces have one or more layers of particulate material placed atop the backing material and spread out over the backing material to surround the grass like fibers. Instrument assembly 100 used in apparatus 2' as disclosed herein need not puncture or penetrate through such a turf surface to measure compaction and thus allows even artificial turf surfaces to be mapped for compaction in the same cost effective, labor saving manner as was true for apparatus 2.

One final difference between apparatus 2' and apparatus 2 is that the drive to arm 10' need not be disconnected over portions of each revolution as was true for arm 10. Drive disconnection at times in each revolution of arm 10 was desirable in part to prevent probes 62 in apparatus 2 from making elongated holes or slots in the ground. However, this problem does not arise from a non-penetrating instrument assembly such as instrument assembly 100. Thus, the clutch control limit switches 86a and 86d can be deleted from apparatus 2'. Clutch 22 can remain in place on apparatus 2' to allow drive to arm 10' to be turned on and off independently of motion of frame 4' using a simple on/off switch to engage or disengage clutch 22.

Various modifications of this invention will be apparent to those skilled in the art. Thus, this invention is not limited to the specific details of the embodiments disclosed herein, but only by the appended claims.

The invention claimed is:

1. A mobile measurement apparatus for measuring a parameter of a turf, soil or ground surface, which comprises:
   (a) a frame supported for movement over the surface;
   (b) an arm carried on the frame for rotation about a first substantially horizontal axis of rotation, the arm having repeating cycles of rotation about the first axis of rotation as the frame is moved over the surface;
   (c) an assembly carried on the arm for rotation about a second substantially horizontal axis of rotation, the assembly rotating in a direction that is opposite to a direction in which the arm is rotating such that the assembly is self-leveling on the arm, the assembly being configured to engage with the surface during each cycle of rotation of the arm; and
   (d) an instrument carried on the assembly for measuring the parameter of the surface from data arising from each engagement of the assembly with the surface.

2. The apparatus of claim 1, wherein the parameter that the instrument is measuring is compaction or hardness of the surface.

3. The apparatus of claim 2, wherein the instrument is a load cell that is acted upon by forces arising from insertion of at least one probe into the surface when the assembly engages the surface.

4. The apparatus of claim 2, wherein the instrument is an accelerometer that measures deceleration of the assembly when the assembly engages the surface.

5. A mobile measurement apparatus for measuring compaction or hardness of a turf, soil or ground surface, which comprises:
   (a) a frame supported for movement over the surface;
   (b) an impact hammer carried on the frame, the hammer being equipped with an instrument for providing data arising from impact of the hammer with the surface which data is indicative of compaction or hardness of the surface;
   (c) a drive carried on the frame and coupled to the hammer for elevating the hammer relative to the frame and for allowing the hammer to vertically drop downwardly relative to the frame under the influence of gravity with a bottom of the hammer impacting against the surface at an end of each drop to provide the compaction or hardness data for a spot on the surface impacted by the hammer, the drive being configured to automatically produce multiple sequential elevations and drops of the hammer in repeating cycles of operation as the frame traverses the surface without requiring the motion of the frame to be stopped and without requiring an operator to manually trigger or initiate the hammer elevations and drops; and
   (d) a motive device other than a walking operator for propelling the frame over the surface in a first longitudinal direction at a predetermined reference speed, and wherein the drive is configured to move the hammer at impact with the surface in a second longitudinal direction that is opposite to the first longitudinal direction and at a speed relative to the surface that is substantially equal to the reference speed of the frame such that the hammer at impact with the surface has substantially zero net longitudinal speed relative to the surface when the frame is traveling at the reference speed.

6. A mobile measurement apparatus for measuring compaction or hardness of a turf, soil or ground surface, which comprises:
   (a) a frame supported for movement over the surface;
   (b) a revolving arm carried on the frame for rotation about a substantially horizontal axis of rotation, the revolving arm being rotated in repeating 360° revolutions about the axis of rotation as the frame is moved over the surface;
   (c) an elongated guide that is rotatably carried on the revolving arm such the elongated guide remains substantially vertical during rotation of the arm; and
   (d) an impact hammer that is vertically slidable on the guide and that is configured to vertically drop downwardly on the guide under the influence of gravity during a first portion of each revolution of the arm such that a bottom of the hammer impacts against the surface once during each revolution of the arm, the hammer being equipped with an instrument for providing data arising from impact of the hammer with the surface which data is indicative of compaction or hardness of the surface.

7. The apparatus of claim 6, wherein the measurement instrument is an accelerometer.

8. The apparatus of claim 6, wherein the hammer is continuously coupled to the guide to continuously move longitudinally with the guide in longitudinal fore-and-aft directions relative to the frame as the guide moves in longitudinal fore-and-aft directions relative to the frame, and wherein the hammer is vertically slidable on the guide during each revolution of the arm even while the hammer is being moved longitudinally by the guide.

9. The apparatus of claim 8, wherein the hammer has a normal lower vertical position on the guide with the hammer being retained in the lower vertical position over a second portion of each revolution of the arm.

10. The apparatus of claim 9, further including a stop carried on the frame with the stop being positioned to be engaged by the hammer at some point in each revolution of the arm, the guide and the arm being arranged to miss the stop such that the guide and arm can continue down past the stop while the hammer is retained atop the stop to cause the hammer to elevate upwardly relative to the guide by virtue of the continued motion of the guide and arm downwardly past the stop.

11. The apparatus of claim 10, wherein the longitudinal motion of the hammer produced by the longitudinal motion of the guide causes the hammer to slide along a length of the stop as the hammer is being elevated with the hammer reaching an edge of the stop when the hammer reaches an elevated upper position on the guide with continued longitudinal motion thereafter causing the hammer to drop off the edge of the stop to fall downwardly along the guide under the influence of gravity to impact against the surface.

12. The apparatus of claim 11, wherein the edge of the stop is located on the frame at a position that allows the hammer to impact against the surface at a bottom dead center position of the arm when the frame is being propelled at a predetermined reference speed, and wherein the hammer is moving in a longitudinal direction and speed that is counter to the direction and speed of motion of the frame at hammer impact such that the hammer has substantially no net longitudinal speed relative to the surface at hammer impact.

13. The apparatus of claim 12, wherein the stop is adjustable on the frame in a longitudinal fore-and-aft manner to longitudinally adjust as need be the position of the edge of the stop on the frame to ensure that hammer impact occurs at the bottom dead center position of the arm when the frame is being propelled at the predetermined reference speed.

14. The apparatus of claim 10, wherein the stop has a compressible cushion that is initially engaged by the hammer when the hammer first hits the stop.

15. The apparatus of claim 6, wherein impact of the hammer with the surface occurs at a bottom dead center position of the arm.

* * * * *